(12) United States Patent
Son et al.

(10) Patent No.: US 7,569,287 B2
(45) Date of Patent: Aug. 4, 2009

(54) BLUE ELECTROLUMINESCENT POLYMER AND ORGANIC ELECTROLUMINESCENT DEVICE USING THE SAME

(75) Inventors: Jhun-Mo Son, Yongin-si (KR); Tae-Yong Noh, Gunpo-si (KR); Sang-Hoon Park, Seongnam-si (KR); Joon-Yong Park, Yongin-si (KR); Tae-Woo Lee, Seoul (KR); Yu-Jin Kim, Suwon-si (KR); In-Nam Kang, Ansan-si (KR)

(73) Assignee: Samsung Mobile Display Co., Ltd., Yongin, Gyunggi-Do (KR)

( * ) Notice: Subject to any disclaimer, the term of this patent is extended or adjusted under 35 U.S.C. 154(b) by 494 days.

(21) Appl. No.: 11/336,868

(22) Filed: Jan. 23, 2006

(65) Prior Publication Data

US 2006/0166037 A1 Jul. 27, 2006

(30) Foreign Application Priority Data

Jan. 21, 2005  (KR) ............... 10-2005-0005811

(51) Int. Cl.
*H01L 51/54* (2006.01)
*H05B 33/14* (2006.01)
*C09K 11/06* (2006.01)
*C07D 265/38* (2006.01)

(52) U.S. Cl. ............... 428/690; 428/917; 313/504; 313/506; 257/40; 257/E51.035; 257/E51.036; 528/7; 528/423

(58) Field of Classification Search ................ 428/690, 428/917; 313/504, 506; 257/40, E51.044, 257/103, E51.026–E51.038; 544/35, 73, 544/102; 546/101; 540/588; 528/423, 7, 528/422

See application file for complete search history.

(56) References Cited

U.S. PATENT DOCUMENTS

| 5,811,834 | A  | * | 9/1998  | Tamano et al. ............ 257/40 |
| 5,879,821 | A  | * | 3/1999  | Hsieh ..................... 428/690 |
| 6,169,163 | B1 |   | 1/2001  | Woo et al. |
| 6,387,544 | B1 | * | 5/2002  | Thompson et al. ........ 428/690 |
| 2003/0218418 | A9 | * | 11/2003 | Sato et al. ................ 313/504 |
| 2004/0072989 | A1 | * | 4/2004  | Son et al. ................. 528/397 |
| 2004/0135131 | A1 | * | 7/2004  | Treacher et al. .......... 252/582 |

FOREIGN PATENT DOCUMENTS

KR   1020030097658   12/2003

* cited by examiner

*Primary Examiner*—Callie E Shosho
*Assistant Examiner*—Michael Wilson
(74) *Attorney, Agent, or Firm*—Robert E. Bushnell, Esq.

(57) ABSTRACT

A blue electroluminescent polymer having a phenoxazine-based unit in a polyarylene backbone and an organic electroluminescent device using the polymer. The organic electroluminescent device has improved luminous efficiency and color purity.

14 Claims, 7 Drawing Sheets

BLUE ELECTROLUMINESCENT POLYMER AND ORGANIC ELECTROLUMINESCENT DEVICE USING THE SAME

CROSS-REFERENCE TO RELATED PATENT APPLICATIONS AND CLAIM OF PRIORITY

This application claims the benefit of Korean Patent Application No. 10-2005-0005811, filed on Jan. 21, 2005, in the Korean Intellectual Property Office, the disclosure of which is incorporated herein in its entirety by reference.

BACKGROUND OF THE INVENTION

1. Field of the Invention

The present invention relates to a blue electroluminescent polymer and an organic electroluminescent device using the same, and more particularly, to a blue electroluminescent polymer having a phenoxazine-based unit in a polyarylene backbone and an organic electroluminescent device having improved luminous efficiency and color purity by using the blue electroluminescent polymer as a light-emitting component.

2. Description of the Related Art

Organic electroluminescent devices are active matrix emission type display devices in which, when an electrical current is applied to a fluorescent or phosphorescent organic compound layer (hereinafter, referred to as an organic layer), electrons and holes are combined in the organic layer to emit light. Organic electroluminescent devices are light and comprise simple components and thus may be manufactured in a simplified process, and also have a wide view angle and high image quality. Further, they can display high quality moving pictures, have high color purity, and can be suitably used for portable electronic devices with low power consumption and low driving voltage.

Such organic electroluminescent devices are classified into low molecular weight organic electroluminescent devices and high molecular weight organic electroluminescent devices depending on a molecular weight of a material used in an organic layer.

In low molecular weight organic electroluminescent devices, an organic layer can be formed by vacuum deposition, the light-emitting materials can be easily purified to a high degree, and color pixels can be easily obtained. For practical applications of the low molecular weight organic electroluminescent devices, however, the quantum efficiency and color purity must be further improved, and crystallization of thin layers must be prevented.

In high molecular weight organic electroluminescent devices, an organic layer can be easily formed by spin coating or printing, so that such polymer organic electroluminescent devices can be manufactured in a simplified manner at low costs. Also, the organic layer exhibits good mechanical properties.

However, high molecular weight organic electroluminescent devices have low color purity and a short lifetime. To overcome these problems. U.S. Pat. No. 6,169,163 describes a method of copolymerizing fluorene-containing polymers to improve electroluminescent characteristics of high molecular weight organic electroluminescent devices. However, the achieved improvement is not satisfactory.

Also, Korean Laid-Open Patent Publication No. 2003-0097658 describes a blue electroluminescent polymer having a phenoxazine unit in a polyarylene backbone and an organic electroluminescent device comprising an organic layer containing the blue electroluminescent polymer. However, the color purity and lifetime of the device should be increased.

Thus, there is an increasing need to develop a phenoxazine monomer in order to improve the color purity while maintaining the lifetime of the device.

SUMMARY OF THE INVENTION

The present invention provides a light-emitting compound which can easily transport charges and is structurally stable, and in particular, has an improved color coordinate characteristic in a blue region due to a phenoxazine monomer contained therein, and an organic electroluminescent device having improved driving characteristics, and in particular, improved color purity by using the light-emitting compound.

According to an aspect of the present invention, there is provided a phenoxazine-based polymer composed of 1 to 99 mol % of a repeating unit having Formula 1 and 99 to 1 mol % of a repeating unit having Formula 2 and having a degree of polymerization of 5 to 2,000:

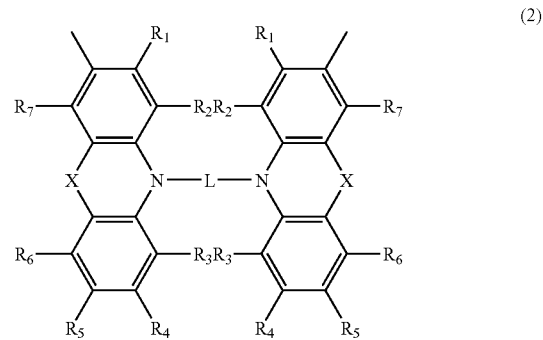

(2)

wherein each of Ar and L is independently selected from the group consisting of a substituted or unsubstituted C6-C30 arylene group and a substituted or unsubstituted C2-C30 heteroarylene group;

each X is independently O, $CH_2$, $CH=CH$, $CH_2-CH_2$, or S; and each of $R_1$ through $R_7$ is independently selected from the group consisting of a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C5-C30 heteroaryl group, a substituted or unsubstituted C5-C30 heteroarylalkyl group, a substituted or unsubstituted C5-C30 heteroaryloxy group, a substituted or unsubstituted C5-C20 cycloalkyl group, and a substituted or unsubstituted C5-C30 heterocycloalkyl group.

According to another aspect of the present invention, there is provided an organic electroluminescent device comprising an organic layer between a pair of electrodes, wherein the organic layer contains the phenoxazine-based polymer.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
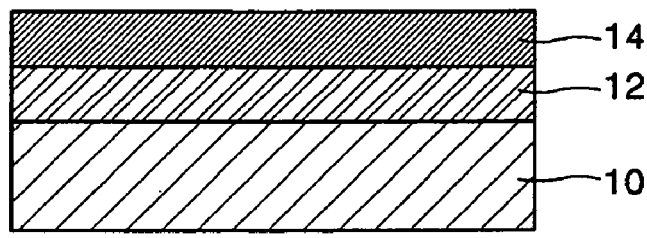
FIGS. 1A through 1F are schematic cross-sectional views of organic electroluminescent devices according to embodiments of the present invention.

Hereinafter, embodiments of the present invention will be described in more detail.

A blue electroluminescent polymer according to an embodiment of the present invention has a structure in which a phenoxazine unit capable of providing a high charge transport capability, particularly hole transport capability, and a blue light-emitting property is introduced into a polyarylene backbone. Due to such a characteristic chemical structure, the blue electroluminescent polymer has an excellent blue light-emitting property.

The phenoxazine-based polymer is composed of 1-99 mol % of a repeating unit having Formula 1 and 99-1 mol % of a repeating unit having Formula 2 and has a degree of polymerization of 5 to 2,000:

$$—Ar— \quad (1)$$

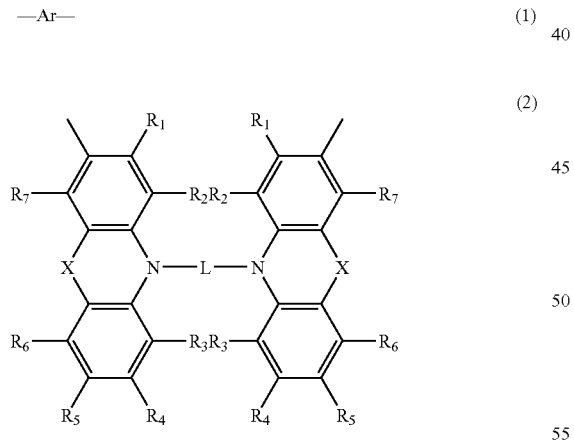

(2)

wherein each of Ar and L is independently selected from the group consisting of a substituted or unsubstituted C6-C30 arylene group and a substituted or unsubstituted C2-C30 heteroarylene group;

each X is independently O, $CH_2$, CH=CH, $CH_2$—$CH_2$, or S; and each of $R_1$ through $R_7$ is independently selected from the group consisting of a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C5-C30 heteroaryl group, a substituted or unsubstituted C5-C30 heteroarylalkyl group, a substituted or unsubstituted C5-C30 heteroaryloxy group, a substituted or unsubstituted C5-C20 cycloalkyl group, and a substituted or unsubstituted C5-C30 heterocycloalkyl group.

The blue electroluminescent polymer may be composed of 80-99 mol % of the repeating unit having Formula 1 and 20-1 mol % of the repeating unit having Formula 2.

The arylene (Ar) unit in Formula 1 and the L unit in Formula 2 may be preferably each independently selected from the following Formulae (1a) through (1q):

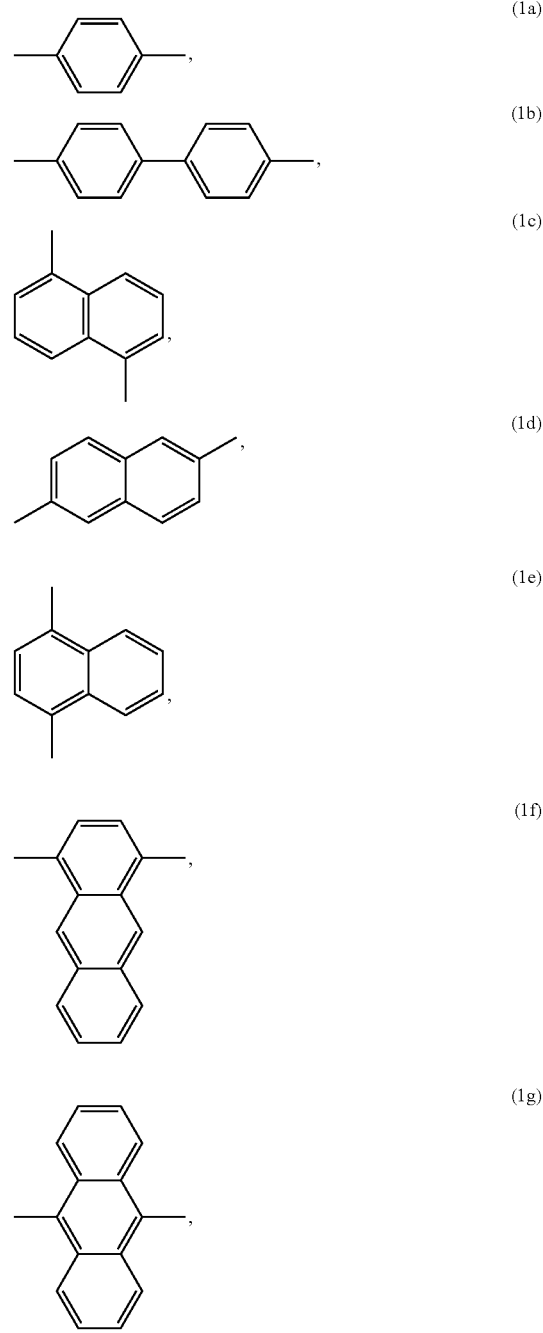

-continued (1h) 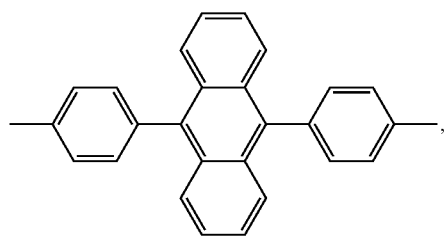

(1i) 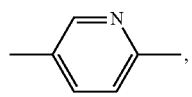

(1j) 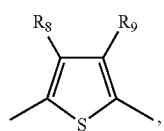

(1k) 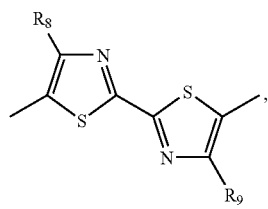

(1l) 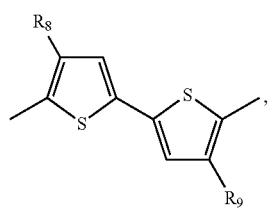

(1m) 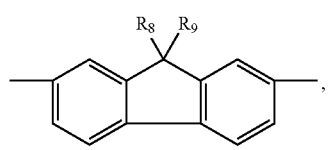

(1n) 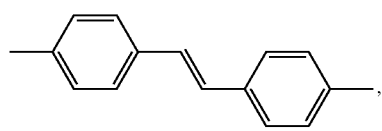

(1o) 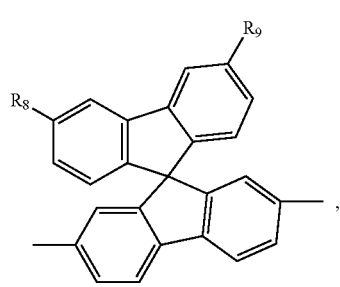

-continued (1p) 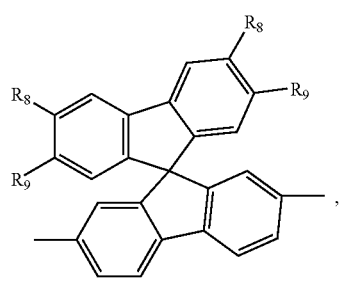

(1q) 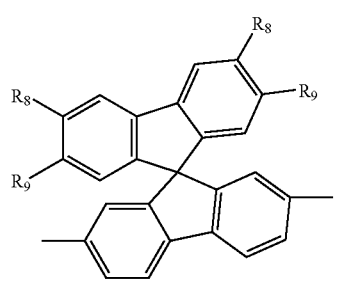

wherein each of $R_8$ and $R_9$ is independently selected from the group consisting of a hydrogen atom, a substituted or unsubstituted C1-C12 alkyl group, a substituted or unsubstituted C1-C12 alkoxy group, and a substituted or unsubstituted amino group.

Preferably, the arylene (Ar) unit composing the backbone of the polymer according to an embodiment of the present invention is represented by the following Formula (1p) having a spirofluorene structure, since this increases thermal stability and prevents formation of an eximer with an adjacent chain, thereby increasing luminous efficiency and color purity:

(1p) 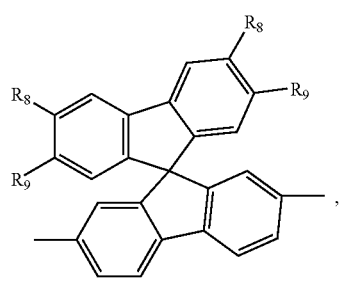

wherein $R_8$ and $R_9$ are as defined above.

Preferably, the L unit in Formula 2 is represented by one of the following Formulae (1a) and (1m), since this increases color purity by controlling a bad gap of the polymer during the polymerization:

(1a) 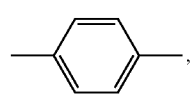

-continued

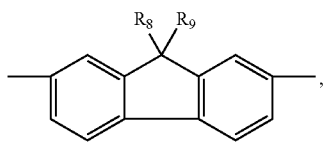

(1m)

wherein $R_8$ and $R_9$ are as defined above.

Specific examples of the polymer according to an embodiment of the present invention include a polymer composed of 1-99 mol % of a repeating unit having Formula 3 and 99-1 mol % of a repeating unit having one of Formulae 4 and 5 and having a degree of polymerization of 5 to 2,000:

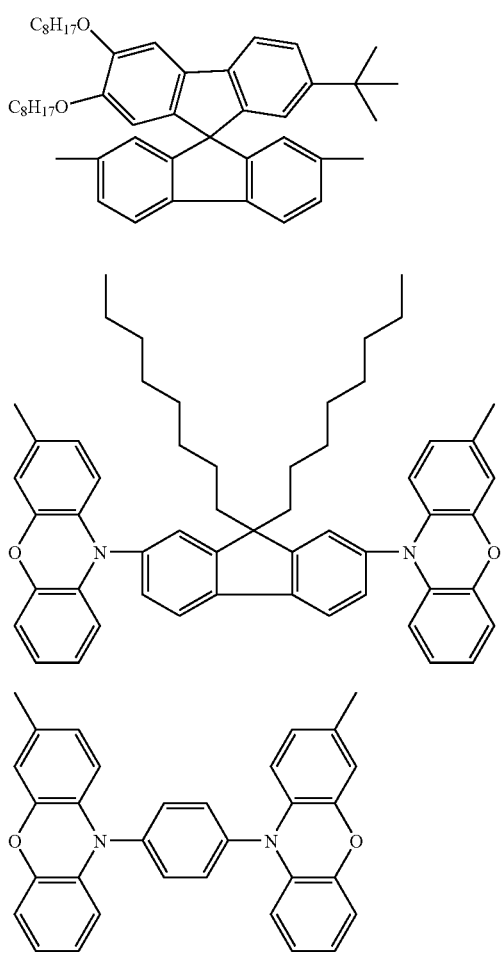

(3)

(4)

(5)

The above polymer may be composed of 80-99 mol % of the repeating unit having Formula 3 and 20-1 mol % of the repeating unit having one of Formulae 4 and 5.

A method of synthesizing a phenoxazine-based polymer in which the Ar unit has the spirofluorene structure according to an embodiment of the present invention will now be described.

First, a phenoxazine-based compound of Formula 10 is synthesized as shown in scheme 1:

Scheme 1

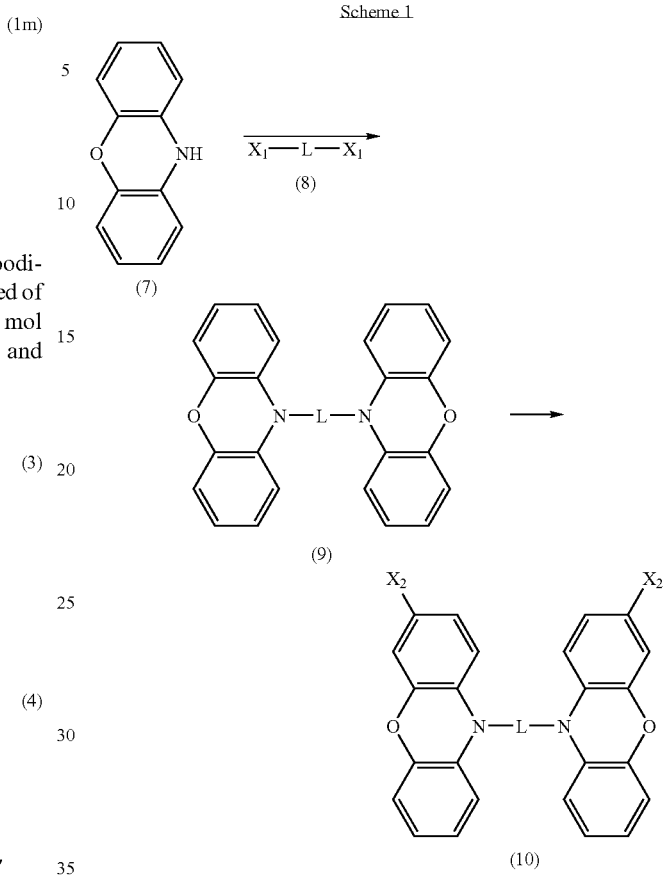

(7)

(8)

(9)

(10)

wherein L is as defined in Formula 2; and
each of $X_1$ and $X_2$ is a halogen atom.

Referring to scheme 1, a phenoxazine derivative of Formula 7 is reacted with a halide of Formula 8 having the L unit, by palladium catalysis (J. Am. Chem. Soc., 1996, 118, 7217 which is incorporated herein by reference), thereby obtaining a compound of Formula 9. Subsequently, the compound C is halogenated by adding an equal equivalent of halogen to the compound of Formula 9 in the presence of a polar organic solvent, for example, chloroform and dimethylformamide, and thus compound of Formula 10 is obtained.

Next, the compound of Formula 10 is polymerized together with the following spirofluorene compound of Formula 11 to obtain the phenoxazine-based polymer:

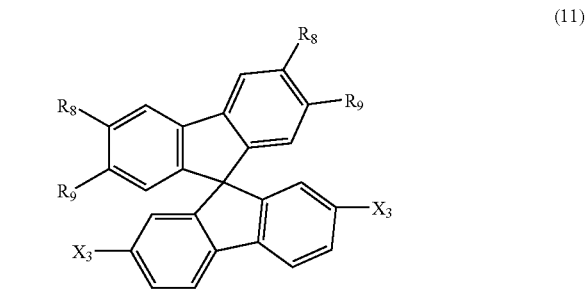

(11)

wherein $R_8$ and $R_9$ are as defined above; and
$X_3$ is a halogen atom.

Other phenoxazine-based polymers according to embodiments of the present invention may be synthesized in a similar way to the method described above.

A weight average molecular weight (Mw) of the blue electroluminescent polymer according to an embodiment of the present invention is an important factor in determining a film forming property of the polymer and a lifetime of an organic electroluminescent device. In the context of the foregoing, the blue electroluminescent polymer may have a weight average molecular weight (Mw) of about 10,000-2,000,000. If the weight average molecular weight (Mw) of the blue electroluminescent polymer is less than 10,000, crystallization can occur in the thin film during the manufacture and driving of the device. If the weight average molecular weight (Mw) of the blue electroluminescent polymer is greater than 2,000,000, it is difficult to manufacture the polymer under conventional synthesis conditions using a Pd(O) or Ni(O)-mediated aryl coupling reaction, and a thin film cannot be easily formed during the manufacture of the organic electroluminescent device.

It is known that a narrower molecular weight distribution (MWD) of a light-emitting polymer is advantageous in view of electroluminescence characteristics (in particular, a lifetime of the device). The blue electroluminescent polymer according to an embodiment of the present invention may have a molecular weight distribution (MWD) of preferably 1.5-5.0, more preferably 1.5-3.0.

Examples of a unsubstituted alkyl group as a substituent in the polymer according to an embodiment of the present invention include methyl, ethyl, propyl, isobutyl, sec-butyl, pentyl, iso-amyl, hexyl, etc., wherein at least one hydrogen atom of the alkyl group may be substituted with a halogen atom, a hydroxy group, a nitro group, a cyano group, a substituted or unsubstituted amino group, such as —$NH_2$, —NH(R) or —N(R')(R") where each of R, R' and R" is independently a C1-C10 alkyl group, an amidino group, hydrazine, hydrazone, a carboxy group, a sulfonic acid group, a phosphoric acid group, a C1-C20 alkyl group, a C1-C20 halogenated alkyl group, a C1-C20 alkenyl group, a C1-C20 alkynyl group, a C1-C20 heteroalkyl group, a C6-C20 aryl group, a C6-C20 arylalkyl group, a C6-C20 heteroaryl group, or a C6-C20 heteroarylalkyl group.

The aryl group as a substituent in the polymer according to an embodiment of the present invention includes a carbocyclic aromatic system containing at least one aromatic ring wherein such aromatic rings may be attached together in a pendent manner or may be fused. Examples of the aryl group include aromatic groups, such as phenyl, naphthyl, and tetrahydronaphthyl, etc. At least one hydrogen atom of the aryl group can be substituted with any substituent described above for the alkyl group.

The heteroaryl group as a substituent in the polymer according to an embodiment of the present invention includes a 5-30 membered aromatic ring system containing one, two, or three hetero atoms selected from N, O, P, and S and having at least one ring wherein such rings may be attached together in a pendent manner or may be fused. At least one hydrogen atom of the heteroaryl group can be substituted with any substituent described above for the alkyl group.

The alkoxy group as a substituent in the polymer according to an embodiment of the present invention includes a radical —O-alkyl wherein the alkyl group is as defined above. Examples of the alkoxy group include methoxy, ethoxy, propoxy, isobutyloxy, sec-butyloxy, pentyloxy, iso-amyloxy, and hexyloxy, etc, wherein at least one hydrogen atom of the alkoxy group can be substituted with any substituent described above for the alkyl group.

The arylalkyl group as a substituent in the polymer according to an embodiment of the present invention includes the above-defined aryl group in which hydrogen atom(s) is substituted with a lower alkyl group, for example, methyl, ethyl, or propyl. Examples of the arylalkyl group include benzyl and phenylethyl, etc. At least one hydrogen atom of the arylalkyl group can be substituted with any substituent described above for the alkyl group.

The heteroarylalkyl group as a substituent in the polymer according to an embodiment of the present invention includes the above-defined heteroaryl group in which hydrogen atom(s) is substituted with a lower alkyl group. At least one hydrogen atom of the heteroarylalkyl group can be substituted with any substituent described above for the alkyl group.

The aryloxy group as a substituent in the polymer according to an embodiment of the present invention includes a radical —O-aryl wherein the aryl group is as defined above. Examples of the aryloxy group include phenoxy, naphthoxy, anthracenyloxy, phenanthrenyloxy, fluorenyloxy, and indenyloxy, etc. At least one hydrogen atom of the aryloxy group can be substituted with any substituent described above for the alkyl group.

The heteroaryloxy group as a substituent in the polymer according to an embodiment of the present invention includes a radical —O-heteroaryl wherein the heteroaryl group is as defined above. Examples of the heteroaryloxy group include benzyloxy and phenylethyloxy, etc. At least one hydrogen atom of the heteroaryloxy group can be substituted with any substituent described above for the alkyl group.

The cycloalkyl group as a substituent in the polymer according to an embodiment of the present invention includes a C5-C30 monovalent monocyclic system wherein at least one hydrogen atom can be substituted with any substituent described above for the alkyl group.

The heterocycloalkyl group as a substituent in the polymer according to an embodiment of the present invention includes a 5-30 membered monovalent cyclic system containing one, two, or three hetero atoms selected from N, O, P, and S. At least one hydrogen atom of the heterocycloalkyl group can be substituted with any substituent described above for the alkyl group.

The amino group as a substituent in the polymer according to an embodiment of the present invention includes —$NH_2$, —NH(R), or —N(R')(R") where each of R, R' and R" is a C1-C10 alkyl group.

An organic electroluminescent device using the blue electroluminescent polymer composed of the repeating unit having Formula 1 and the repeating unit having Formula 2 according to an embodiment of the present invention and a method of manufacturing the device will now be described.

FIGS. 1A through 1F are schematic cross-sectional views illustrating laminated structures of organic electroluminescent devices according to embodiments of the present invention.

Referring to FIG. 1A, a light-emitting layer 12 containing the blue electroluminescent polymer is formed on a first electrode 10 and a second electrode 14 is formed on the light-emitting layer 12.

Figure 1B:
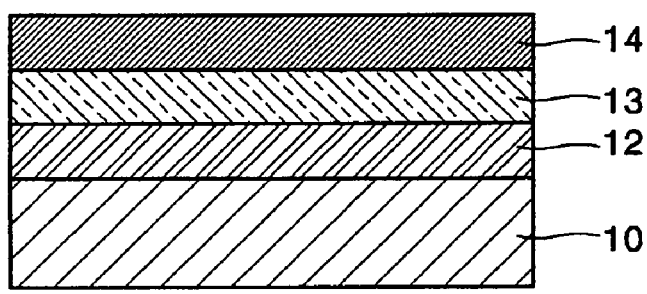

Referring to FIG. 1B, a light-emitting layer 12 containing the blue electroluminescent polymer is formed on a first electrode 10, a hole blocking layer (HBL) 13 is formed on the light-emitting layer 12, and a second electrode 14 is formed on the HBL 13.

Figure 1C:
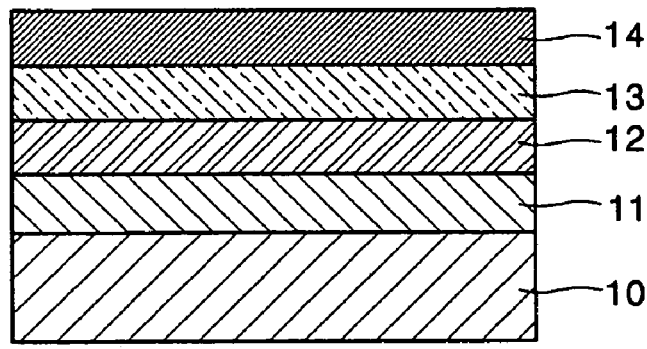

An organic electroluminescent device illustrated in FIG. 1C has the same laminated structure as that illustrated in FIG. 1B, except that a hole injection layer (HIL) 11 (also referred to as a buffer layer) is further formed between a first electrode 10 and a light-emitting layer 12.

Figure 1D:
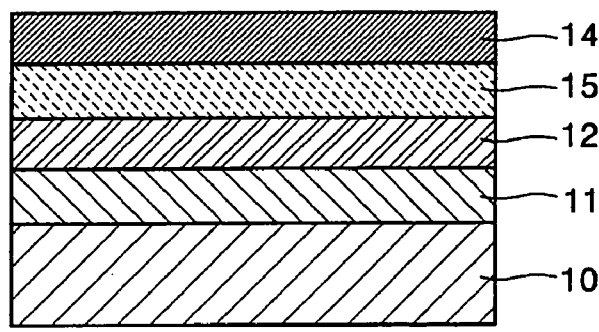

An organic electroluminescent device illustrated in FIG. 1D has the same laminated structure as that illustrated in FIG. 1C, except that an electron transport layer (ETL) 15, instead of the HBL 13, is formed on the light-emitting layer 12.

Figure 1E:
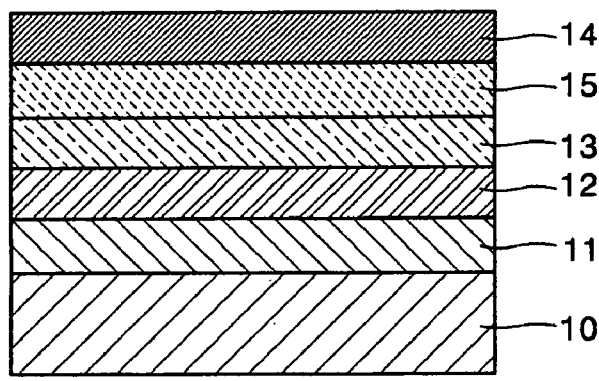

An organic electroluminescent device illustrated in FIG. 1E has the same laminated structure as that illustrated in FIG. 1C, except that a double layer having an HBL 13 and an ETL 15 sequentially laminated, instead of the HBL 13, is formed on the light-emitting layer 12.

Figure 1F:
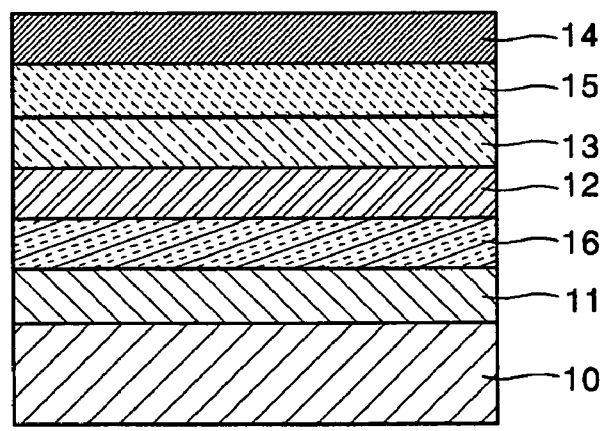

An organic electroluminescent device illustrated in FIG. 1F has the same laminated structure as that illustrated in FIG. 1E, except that a hole transport layer (HTL) 16 is further formed between the HIL 11 and the light-emitting layer 12. Holes generated in the first electrode move to the light-emitting layer through the hole injection layer 11 and the hole transport layer 16, and electrons generated in the second electrode move to the light-emitting layer through the electron transport layer 15. The HTL 16 prevents impurities in the HIL 11 from penetrating into the light-emitting layer 12.

The organic electroluminescent device according to an embodiment of the present invention may be manufactured by, conventional methods. However, other method way be used A method of manufacturing an organic electroluminescent device according to an embodiment of the present invention will now be described.

First, a first electrode 10 is patterned on a substrate (not shown). The substrate is a conventional substrate used in an organic electroluminescent device and may be a glass substrate or a transparent plastic substrate, which has excellent transparency, surface smoothness, easy handling, and excellent waterproofness. The substrate may have a thickness of 0.3-1.1 mm.

When the first electrode 10 is an anode, it is made of a conductive metal capable of easily injecting holes or an oxide thereof. Examples of the material for the first electrode 10 include ITO (ilndium tin oxide), IZO (indium zinc oxide), nickel (Ni), platinum (Pt), gold (Au) and iridium (Ir).

The substrate having the first electrode 10 formed thereon is cleaned, and then treated with $UV/O_3$. When in cleaning the substrate, an organic solvent such as isopropanol (IPA) or acetone is used.

An HIL 11 is selectively formed on the first electrode 10 of the cleaned substrate. When the HIL 11 is formed on the first electrode 10, a contact resistance between the first electrode 10 and a light-emitting layer 12 decreases and a capability of the first electrode 10 to transport holes to the light-emitting layer 12 increases, thereby improving the driving voltage and lifetime of the device. A material for forming the HIL 11 may be any material commonly used in the art. Examples of the material for forming the HIL 11 include poly(3,4-ethylenedioxythiophene) (PEDOT)/polystyrene parasulfonate (PSS), starburst materials, copper phthalocyanine, polythiophene, polyaniline, polyacetylene, polypyrrole, polyphenylene vinylene, or derivatives of these compounds. The material for the HIL 11 is spin coated on the first electrode 10 and dried, thereby forming an HIL 11. The HIL 11 may have a thickness of 300-2000 Å, preferably 500-1100 Å. If the thickness of the HIL 11 is not in the range specified above, the hole injection capability is poor. The drying may be performed at 100-250° C.

The light-emitting layer 12 is formed by spin coating a composition for forming a light-emitting layer on the HIL 11 and drying the coating. The light-emitting layer forming composition comprises 0.5-20% by weight of the blue electroluminescent polymer according to an embodiment of the present invention and 99.5-80% by weight of a solvent.

Any solvent that can dissolve the light-emitting polymer can be used as the solvent in the composition. Examples of the solvent include toluene, chlorobenzene, xylene, etc.

In some cases, the light-emitting layer forming composition may further comprise a dopant. The concentration of the dopant in the composition varies according to a material for forming the light-emitting layer 12, and may be 30-80 parts by weight based on 100 parts by weight of the material for the light-emitting layer 12 (i.e., based on 100 parts by weight of a total of a host and a dopant). If the concentration of the dopant is not in the range specified above, the light-emitting property of the electroluminescent device deteriorates. Examples of the dopant include arylamine, a peryl compound, a pyrrole compound, a hydrazone compound, a carbazole compound, a stilbene compound, a starburst compound, an oxadiazole compound, etc.

A thickness of the light-emitting layer 12 may be adjusted to be 100-1000 Å, preferably 500-1000 Å, by controlling the concentration of the light-emitting layer forming composition and the spin speed during the spin coating. If the thickness of the light-emitting layer 12 is less than 100 Å, a luminous efficiency of the device decreases. If the thickness of the light-emitting layer 12 is greater than 1000 Å, the driving voltage of the device increases.

An HTL 16 may be selectively formed between the HIL 11 and the light-emitting layer 12. Any material having hole transporting capability can be used as a material for forming the HTL 16. Examples of the material for forming the HTL 16 include polytriphenylamine, etc. The HTL 16 may have a thickness of 100-1000 Å.

An HBL 13 and/or an ETL 15 may be formed on the light-emitting layer 12 by evaporation or spin coating. The HBL 13 prevents excitons formed in the light-emitting material from moving to the ETL 15 or prevents holes from moving to the ETL 15.

Examples of a material for forming the HBL 13 include LiF, $BaF_2$, $MgF_2$, a phenanthroline compound of Formula 12, e.g., BCP manufactured by UDC Co., Ltd., an imidazole compound of Formula 13, a triazole compound of Formula 14, an oxadiazole compound of Formula 15, e.g., PBD, and an aluminum complex manufactured by UDC Co., Ltd., and Balq represented by Formula 16:

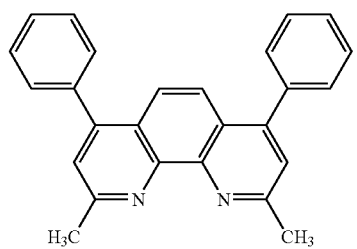

(12)

Phenanthroline-containing organic compound (13)

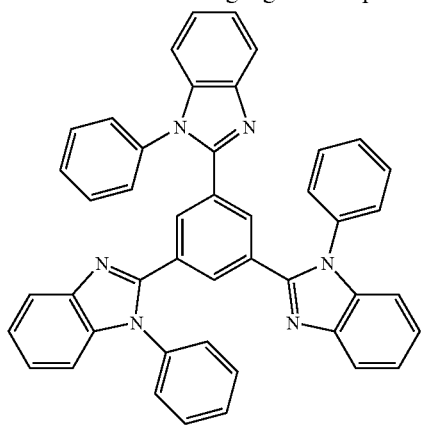

Imidazole-containing organic compound (14)

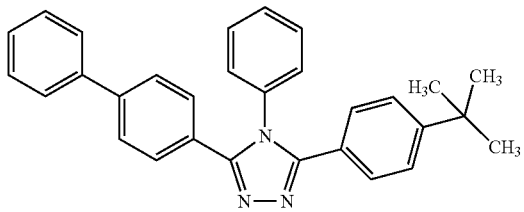

Triazole-containing organic compound (15)

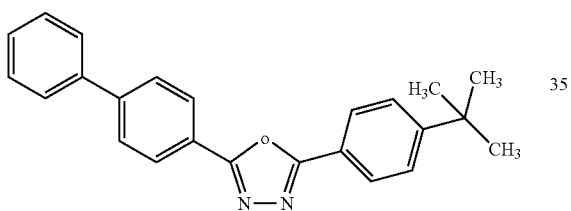

Oxadiazole-containing organic compound (16)

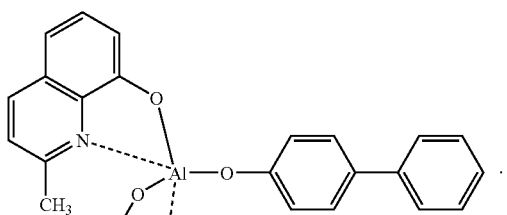

BAlq

Gaq'2OPiv of Formula 21, Gaq'2OAc of Formula 22, or 2(Gaq'2), represented by Formula 23:

(17)

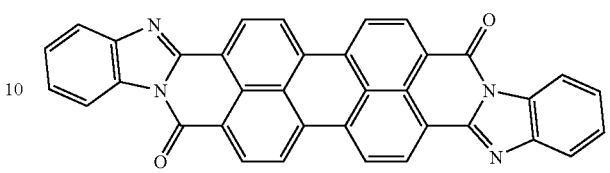

Perylene compound (18)

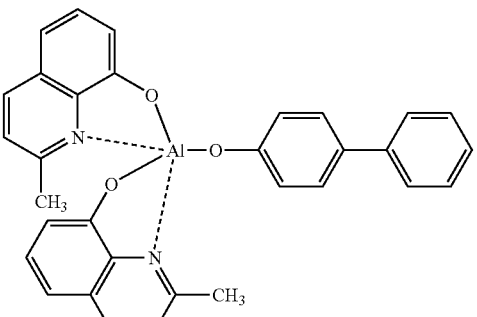

Alq3

(16)

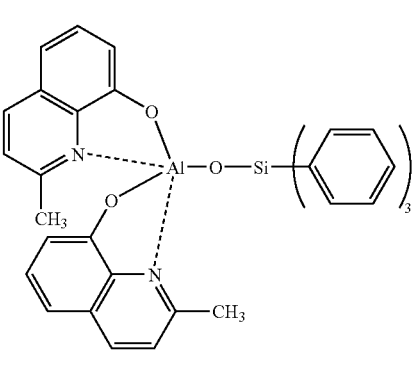

BAlq (19)

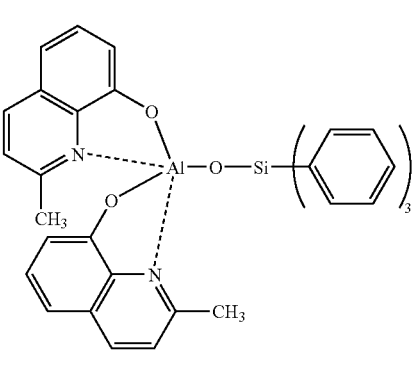

SAlq

Examples of a material for forming the ETL 15 include an oxazole compound, an isoxazole compound, a triazole compound, an isothiazole compound, an oxadiazole compound, a thiadiazole compound, a perylene compound of Formula 17, an aluminum complex, e.g., Alq3 (tris(8-quinolinolato)-aluminum) of Formula 18, BAlq of Formula 16, SAlq of Formula 19, or Almq3 of Formula 20, and a gallium complex, e.g., -continued

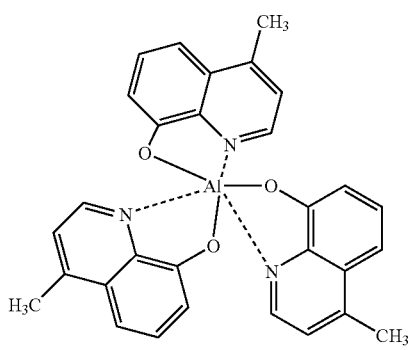

Almq3

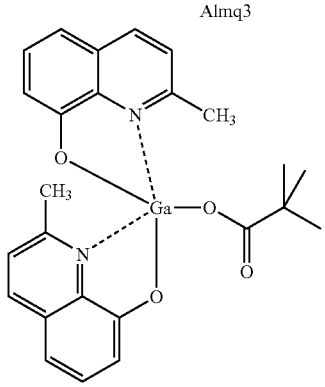

Gaq'2OPiv

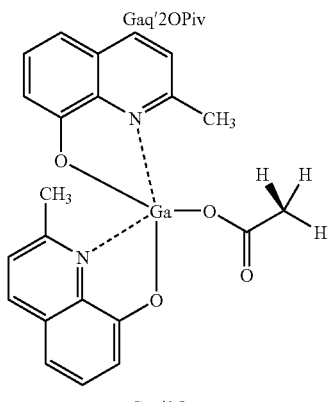

Gaq'2Oac

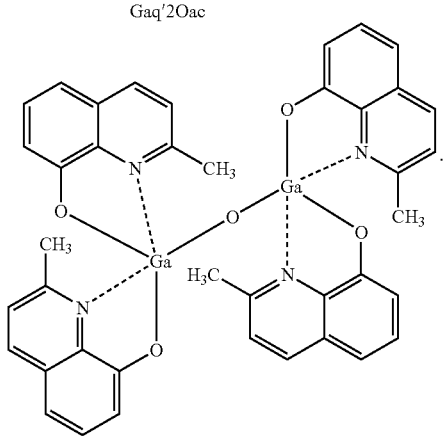

2(Gaq'2)

(20)

(21)

(22)

(23)

The HBL 13 may have a thickness of 100-1000 Å, and the ETL 15 may have a thickness of 100-1000 Å. If the thicknesses of the HBL 13 and the ETL 15 are not in the ranges specified above, hole blocking capability and electron transport capability are poor.

Then, a second electrode 14 is formed on the resultant product, followed by encapsulating, thereby completing an organic electroluminescent device.

A material for forming the second electrode 14 is not specifically limited and the second electrode 14 may be formed by depositing a metal having a low work function, for example, Li, Ca, Ca/Al, LiF/Ca, BaF$_2$/Ca, LiF/Al, Al, Mg, and Mg alloy. The second electrode 14 may have a thickness of 50-3000 Å.

The polymer according to an embodiment of the present invention may be used not only as the material for forming a light-emitting layer in manufacturing the organic electroluminescent device, but also as the material for forming an HTL. Also, the polymer may be used as an intermediate in bio-field.

The organic electroluminescent device according to an embodiment of the present invention may be manufactured by conventional methods using a light-emitting polymer, without a need for any special apparatus or method.

Hereinafter, the present invention will be described in more detail with reference to the following examples. However, these examples are given for the purpose of illustration and are not intended to limit the scope of the invention.

SYNTHESIS EXAMPLE 1

Preparation of Polymer Composed of Repeating Units of Formulae 3 and 4

A Schlenk flask was evacuated and refluxed with nitrogen gas several times to completely remove moisture. Then, 660 mg (2.4 mmol) of bis(1,5-cyclooctadiene)nickel(O) [hereinafter, referred to as Ni(COD)] and 300 mg (1.9 mmol) of bipyridal were charged into the Schlenk flask in a glove box, and the flask was evacuated and refluxed with nitrogen gas several times again. Next, 5 ml of anhydrous dimethylformamide, 259 mg (3.2 mmol) of 1,5-cyclooctadiene (COD), and 5 ml of anhydrous toluene were added to the flask under a nitrogen stream. After the mixture was stirred at 80° C. for 30 min, 556 mg (0.072 mmol) of the compound of Formula 3 and 73 mg (0.008 mmol) of the compound of Formula 4 were diluted with 5 ml of toluene and added to the mixture. Next, 5 ml of toluene was added to the mixture while washing materials adhered to the flask wall, and then the mixture was stirred at 80° C. for 24 hours.

After the reaction was completed, the temperature of the reaction mixture was cooled to room temperature. Then, the reaction mixture was poured into a mixture of HCl, acetone, and methanol (volume ratio 1:1:2) to form precipitates. The precipitates thus formed were dissolved in chloroform, and then re-precipitated in methanol. Then, the resultant product was treated with a Soxhlet extractor to obtain 0.32 mg of TBDAFP91 (poly(2',3'-dioctyloxy-6'-t-butylspirofluorene-co-2,7-bis(N-phenoxazinyl)-9,9-dioctylfluorene) (mole ratio 90:10)). The obtained polymer was analyzed by gel permeation chromatography (GPC). The GPC analysis revealed that the weight average molecular weight (Mw) was 150,000 and the molecular weight distribution (MWD) was 2.63.

SYNTHESIS EXAMPLE 2

Preparation of Polymer Composed of Repeating Units of Formulae 3 and 5

A Schlenk flask was evacuated and refluxed with nitrogen gas several times to completely remove moisture. Then, 660 mg (2.4 mmol) of Ni(COD) and 300 mg (1.9 mmol) of bipyridal were charged into the Schlenk flask in a glove box, and the flask was evacuated and refluxed with nitrogen gas several times again. Next, 5 ml of anhydrous dimethylformamide, 259 mg (3.2 mmol) of 1,5-cyclooctadiene (COD), and 5 ml of anhydrous toluene were added to the flask under a nitrogen stream. After the mixture was stirred at 80° C. for 30 min, 556 mg (0.072 mmol) of the compound of Formula 3 and 24 mg (0.008 mmol) of the compound of Formula 5 were diluted with 5 ml of toluene and added to the mixture. Next, 5 ml of toluene was added to the mixture while washing materials adhered to the flask wall, and then the mixture was stirred at 80° C. for 24 hours.

After the reaction was completed, the temperature of the reaction mixture was cooled to room temperature. Then, the reaction mixture was poured into a mixture of HCl, acetone, and methanol (volume ratio 1:1:2) to form precipitates. The precipitates thus formed were dissolved in chloroform, and then re-precipitated in methanol. Then, the resultant product was treated with a Soxhlet extractor to obtain 0.32 mg of TBDBzP91 (poly(2',3'-dioctyloxy-6'-t-butylspirofluorene-co-1,4-bis(N-phenoxazinyl)benzene)). The obtained polymer was analyzed by GPC. The GPC analysis revealed that the weight average molecular weight (Mw) was 120,000 and the molecular weight distribution (MWD) was 2.24.

Figure 2:
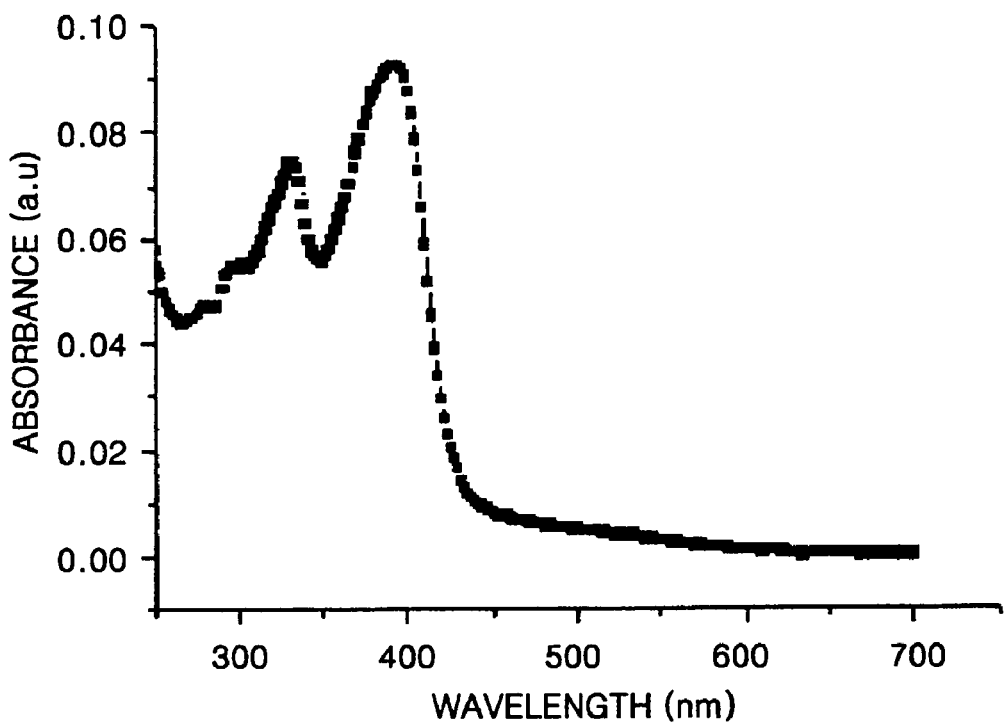
FIGS. 2 and 3 are respectively a UV absorption spectrum and a photoluminescent spectrum of the polymer obtained in Synthesis Example 1.
Figure 3:
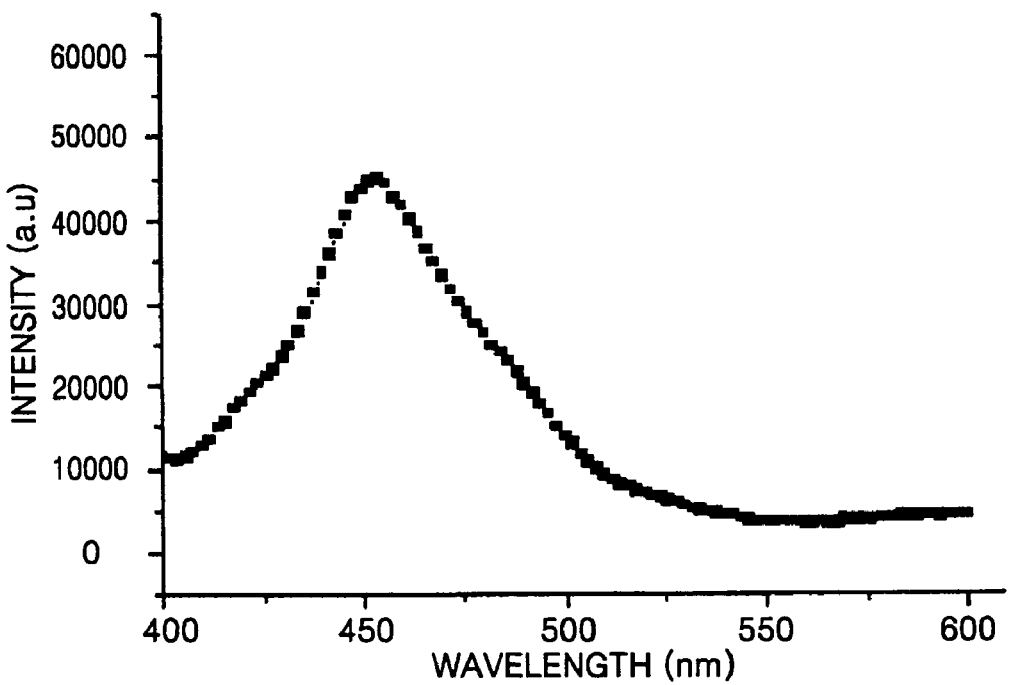
Figure 4:
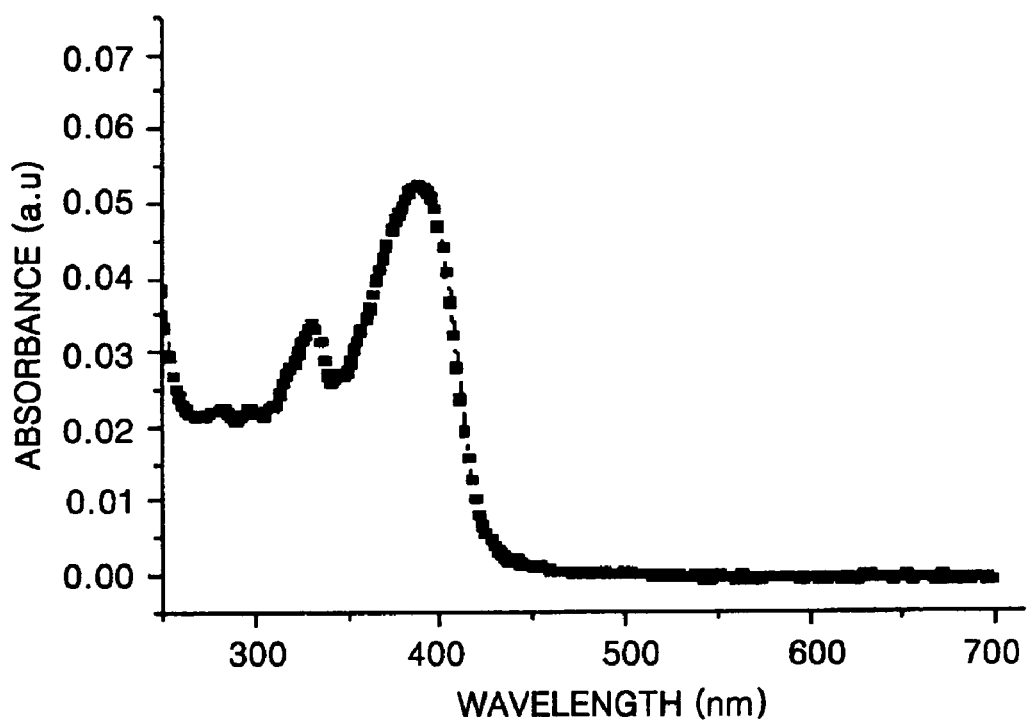
FIGS. 4 and 5 are respectively a UV absorption spectrum and a photoluminescent spectrum of the polymer obtained in Synthesis Example 2.
Figure 5:
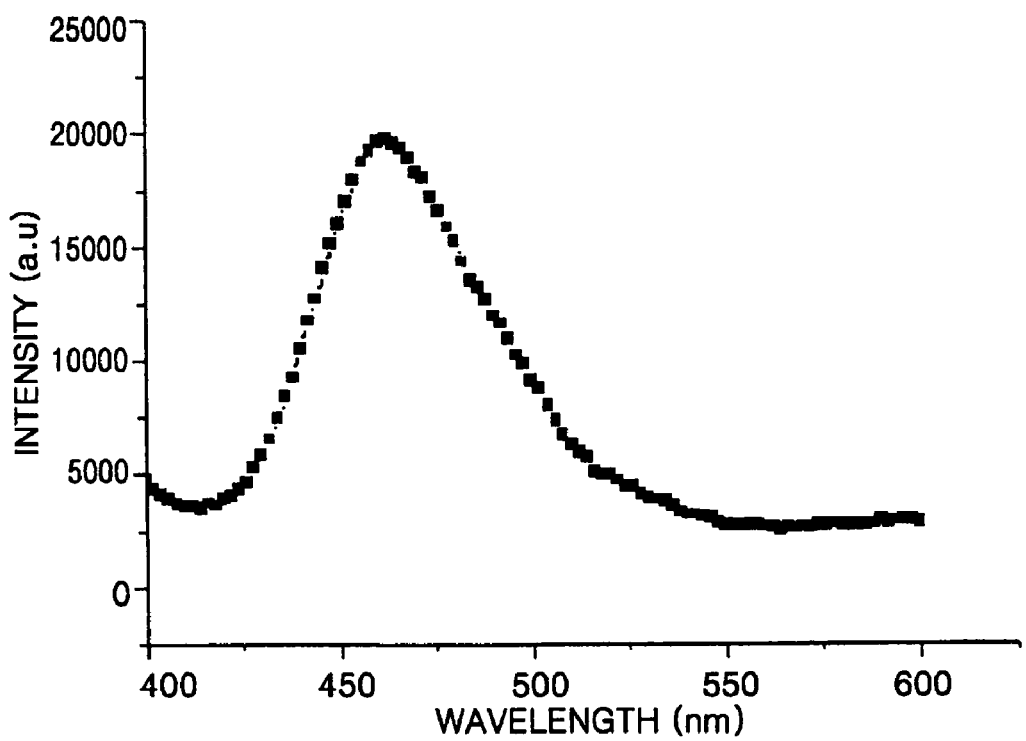

The UV absorption spectrums and photoluminescent spectrums of the polymers obtained in Synthesis Examples 1 and 2 were examined and illustrated in FIGS. 2 through 5. FIGS. 2 and 3 are respectively a UV absorption spectrum and a photoluminescent spectrum of the polymer obtained in Synthesis Example 1, and FIGS. 4 and 5 are respectively a UV absorption spectrum and a photoluminescent spectrum of the polymer obtained in Synthesis Example 2.

Referring to FIGS. 2 through 5, the polymers obtained in Synthesis Examples 1 and 2 had blue electroluminescent characteristics. These polymers had a high color purity of (0.14, 0.20).

EXAMPLE 1

Manufacture of Organic Electroluminescent Device

An electroluminescent device was manufactured using the polymer obtained in Synthesis Example 1.

First, a transparent electrode substrate of glass coated with ITO (indium tin oxide) was cleaned. Then, the ITO was patterned by using a photoresist resin and an etchant, and the resulting substrate was cleaned again. Batron P 4083 (available from Bayer) as a conductive buffer layer was coated onto the substrate to a thickness of about 800 Å, and then baked at 180° C. for about 1 hour. A composition for forming a light-emitting layer was prepared by dissolving 1 part by weight of the polymer obtained in Synthesis Example 1 in 99 parts by weight of toluene, and then filtering through a 0.2 mm filter. The composition was spin coated on the above buffer layer. After baking the coated substrate, the solvent was removed in a vacuum oven to form a thin electroluminescent polymeric film. In the spin coating, the thickness of the thin polymeric film was adjusted to about 80 nm by controlling the concentration of the polymer solution and the spin speed.

$BaF_2$, Ca, and Al were sequentially deposited on the thin polymeric film using a vacuum depositor under a vacuum of $4 \times 10^{-6}$ torr or less. When depositing, the thickness and the growth rate of the thin film were controlled using a crystal sensor.

EXAMPLE 2

Manufacture of Organic Electroluminescent Device

An organic electroluminescent device was manufactured in the same manner as in Example 1, except that the polymer obtained in Synthesis Example 2 was used instead of the polymer obtained in Synthesis Example 1.

Figure 6:
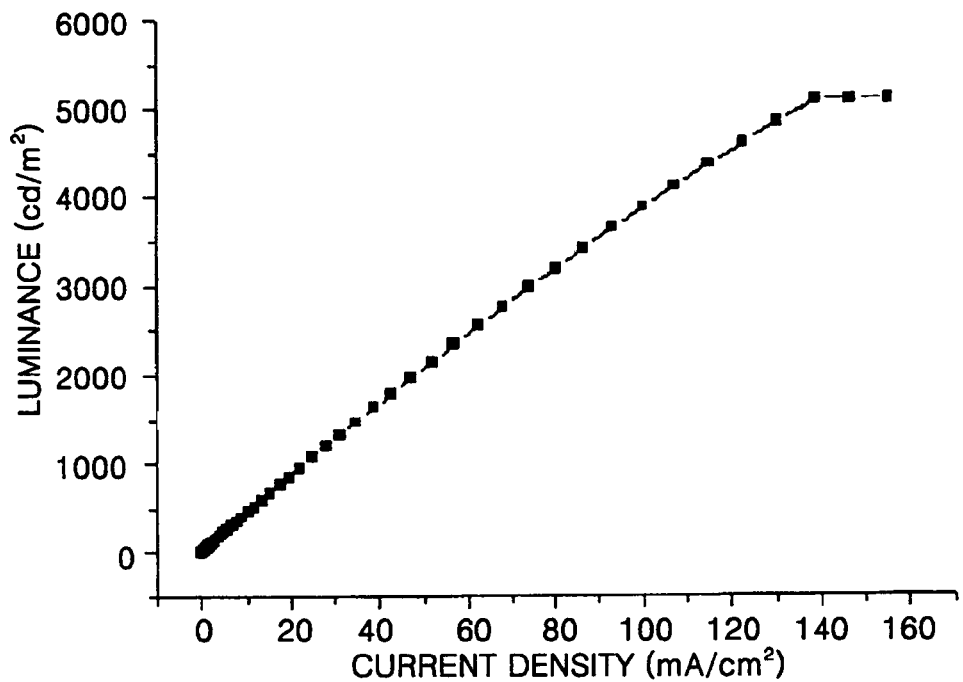
FIG. 6 is a graph of current density vs. luminance for the organic electroluminescent device obtained in Example 1.
Figure 7:
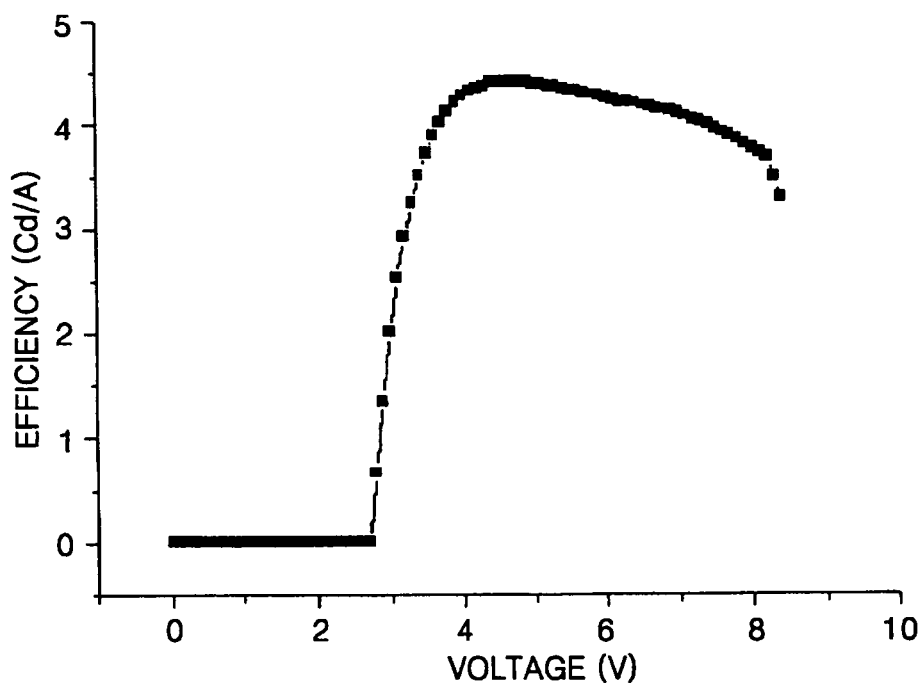
FIG. 7 is a graph of voltage vs. efficiency for the organic electroluminescent device obtained in Example 1.
Figure 8:
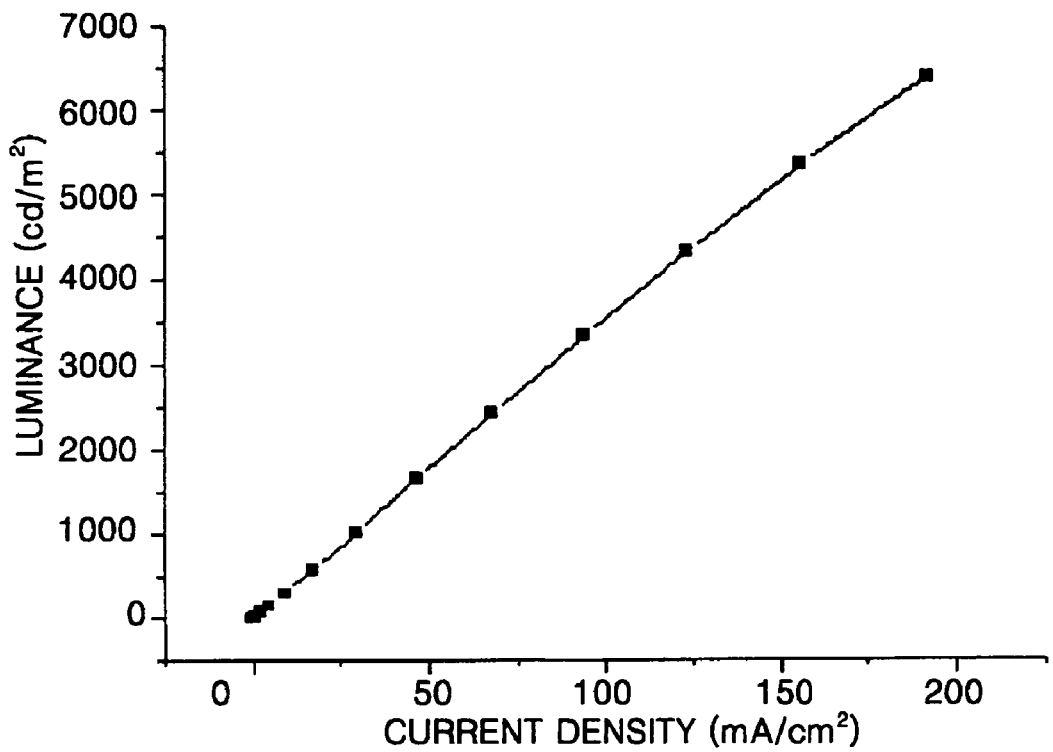
FIG. 8 is a graph of current density vs. luminance for the organic electroluminescent device obtained in Example 2.
Figure 9:
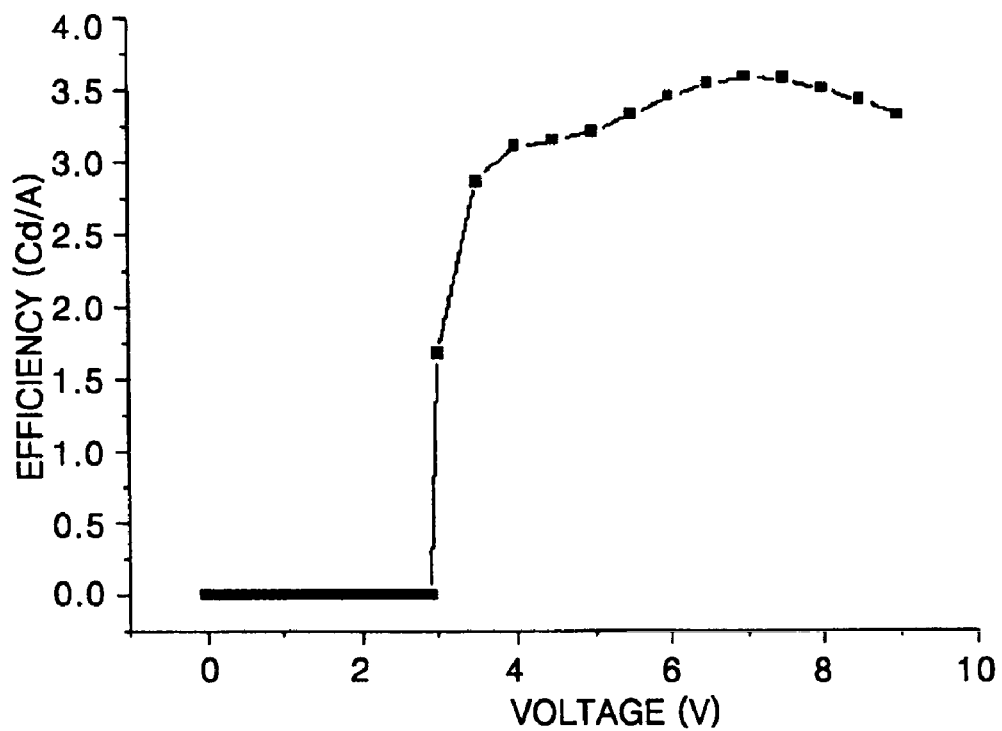
FIG. 9 is a graph of voltage vs. efficiency for the organic electroluminescent device obtained in Example 2.

The luminance and efficiency of the organic electroluminescent device manufactured in Example 1 were evaluated and illustrated in FIGS. 6 and 7, respectively. Also, the luminance and efficiency of the organic electroluminescent device manufactured in Example 2 were evaluated and illustrated in FIGS. 8 and 9, respectively. In the evaluation, the forward bias voltage as a direct voltage was used for the driving voltage. The devices showed typical properties of rectifying diodes. Especially, the devices showed excellent stability, in that the initial voltage-current density characteristics were maintained even after driving had been repeated several times.

Referring to FIGS. 6 through 9, the organic electroluminescent devices manufactured in Examples 1 and 2 had excellent luminance and efficiency.

Figure 10:
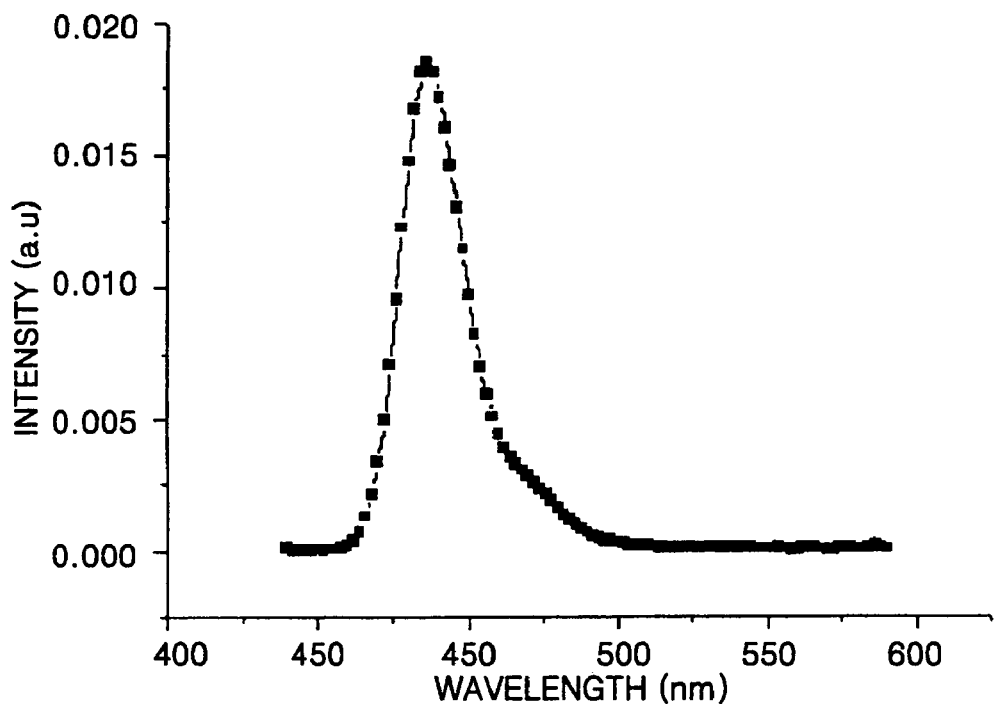
FIG. 10 is an electroluminescent spectrum of the organic electroluminescent device obtained in Example 1.
Figure 11:
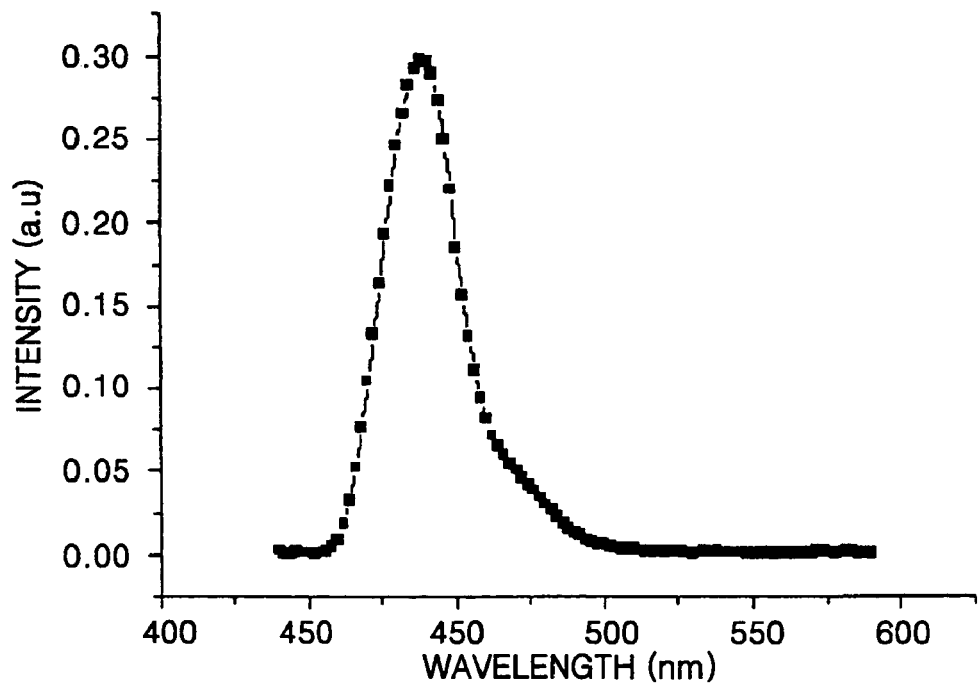
FIG. 11 is an electroluminescent spectrum of the organic electroluminescent device obtained in Example 2.

FIGS. 10 and 11 are electroluminescent spectrums of the organic electroluminescent devices manufactured in Examples 1 and 2. Referring to FIGS. 10 and 11, the devices exhibited high purity blue light-emitting properties. In particular, the devices had constant color purity even though the voltage changed, and had good color stability.

As described above, a phenoxazine-based polymer according to the present invention has a blue electroluminescent property. The phenoxazine-based polymer can be easily prepared and has a blue light-emitting property. An organic electroluminescent device having an organic layer containing the phenoxazine-based polymer according to the present invention has improved color purity, efficiency, and luminance.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A polymer comprised of 1 to 99 mol % of a repeating unit having Formula (1) and 99 to 1 mol % of a repeating unit having Formula (2), the polymer having a degree of polymerization of 5 to 2,000:

—Ar— (1)

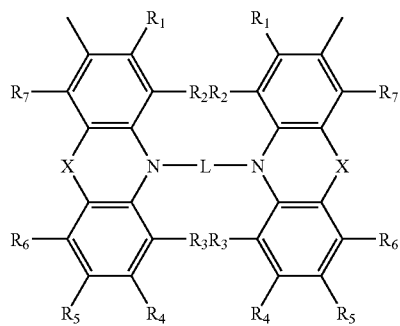

wherein Ar is independently selected from the group consisting of a substituted or unsubstituted C6-C30 arylene group and a substituted or unsubstituted C2-C30 heteroarylene group;

L is selected from the group consisting of the following formulas;

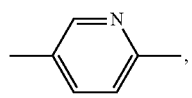 (1i)

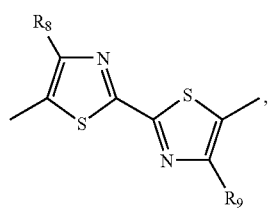 (1k)

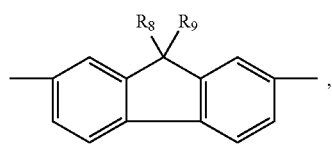 (1m)

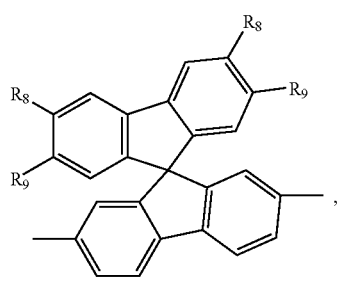 (1p)

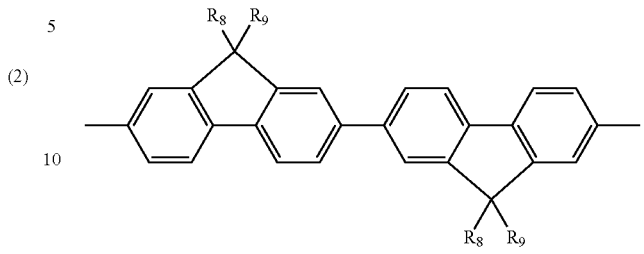 (1q)

wherein each of $R_8$ and $R_9$ is independently selected from the group consisting of a hydrogen atom, a substituted or unsubstituted C1-C12 alkyl group, a substituted or unsubstituted C1-C12 alkoxy group, and a substituted or unsubstituted amino group;

each X is $CH_2$—$CH_2$; and each of $R_1$ through $R_7$ is independently selected from the group consisting of a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C5-C30 heteroaryl group, a substituted or unsubstituted C5-C30 heteroarylalkyl group, a substituted or unsubstituted C5-C30 heteroaryloxy group, a substituted or unsubstituted C5-C20 cycloalkyl group, and a substituted or unsubstituted C5-C30 heterocycloalkyl group.

2. The polymer of claim 1, wherein the arylene (Ar) unit in the Formula (1) is represented by one selected from the group consisting of Formulae (1i), (1k), (1o) and (1q)

 (1i)

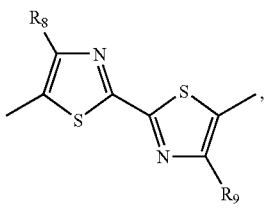 (1k)

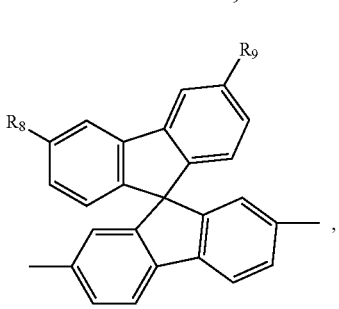 (1o)

-continued

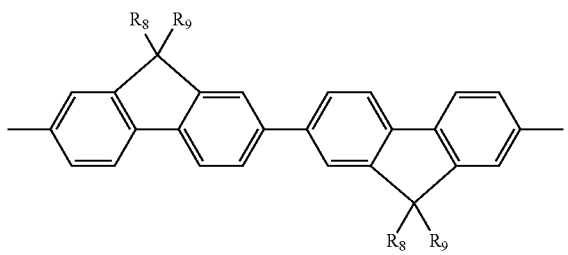
(1q)

wherein each of $R_8$ and $R_9$ is independently selected from the group consisting of a hydrogen atom, a substituted or unsubstituted C1-C12 alkyl group, a substituted or unsubstituted C1-C12 alkoxy group, and a substituted or unsubstituted amino group.

3. The polymer of claim 1, wherein the Ar unit in the Formula (1) is represented by Formula (1p):

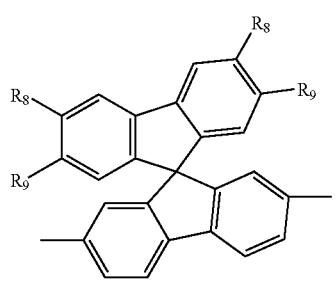
(1p)

wherein each of $R_8$ and $R_9$ is independently selected from the group consisting of a hydrogen atom, a substituted or unsubstituted C1-C12 alkyl group, a substituted or unsubstituted C1-C12 alkoxy group, and a substituted or unsubstituted amino group.

4. The polymer of claim 1, wherein the L unit in the Formula (2) is represented by Formula (1m):

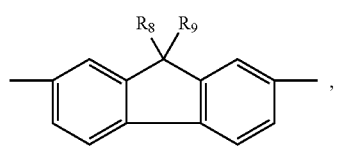
(1m)

wherein each of $R_8$ and $R_9$ is independently selected from the group consisting of a hydrogen atom, a substituted or unsubstituted C1-C12 alkyl group, a substituted or unsubstituted C1-C12 alkoxy group, and a substituted or unsubstituted amino group.

5. The polymer of claim 1, having a weight average molecular weight (Mw) of 10,000-2,000,000 and a molecular weight distribution (MWD) of 1.5 to 3.0.

6. The polymer of claim 1, which is comprised of 80 to 99 mol % of the repeating unit having the Formula (1) and 1 to 20 mol % of the repeating unit having the Formula (2).

7. An organic electroluminescent device comprising an organic layer containing the polymer of claim 1.

8. The organic electroluminescent device of claim 7, wherein the organic layer is a light-emitting layer or a hole transport layer.

9. The organic electroluminescent device of claim 7, wherein the Ar unit in the Formula (1) is represented by Formula (1p) and the L unit in the Formula (2) is represented by Formula (1m):

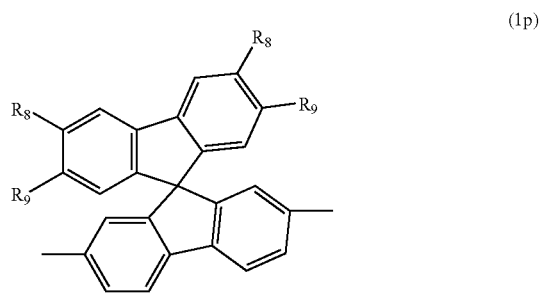
(1p)

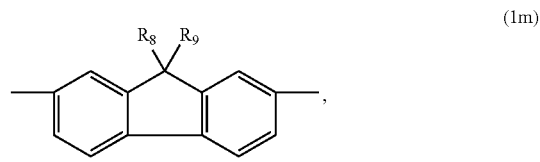
(1m)

wherein each of $R_8$ and $R_9$ is independently selected from the group consisting of a hydrogen atom, a substituted or unsubstituted C1-C12 alkyl group, a substituted or unsubstituted C1-C12 alkoxy group, and a substituted or unsubstituted amino group.

10. The organic electroluminescent device of claim 7, wherein the Ar unit in the Formula 1 has a spirofluorene structure.

11. The organic electroluminescent device of claim 7, wherein the polymer has a weight average molecular weight (Mw) of 10,000 to 2,000,000 and a molecular weight distribution (MWD) of 1.5 to 3.0.

12. A polymer comprised of 1 to 99 mol % of a repeating unit having Formula (3) and 99 to 1 mol % of a repeating unit having Formula (4):

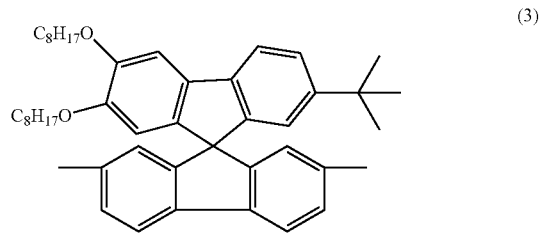
(3)

-continued (4)

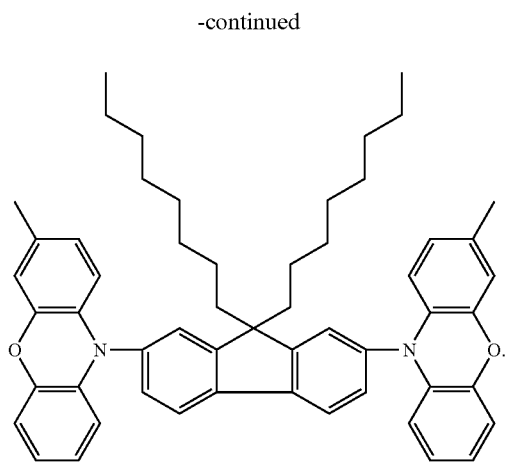

13. The polymer of claim 12, having a weight average molecular weight (Mw) of 10,000 to 2,000,000 and a molecular weight distribution of 1.5 to 3.0.

14. A polymer comprised of 1 to 99 mol % of a repeating unit having Formula (1) and 99 to 1 mol % of a repeating unit having Formula (2), the polymer having a degree of polymerization of 5 to 2,000:

—Ar— (1)

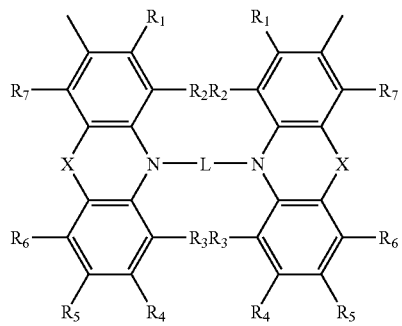

(2)

wherein L is selected from the group consisting of a substituted or unsubstituted C6-C30 arylene group and a substituted or unsubstituted C2-C30 heteroarylene group;

Ar is selected from the group consisting of the following formulas:

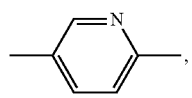

(1i)

-continued

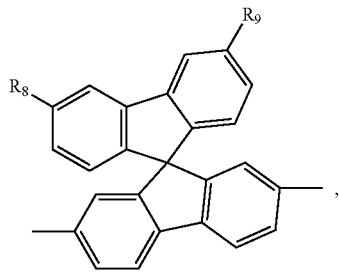

(1k)

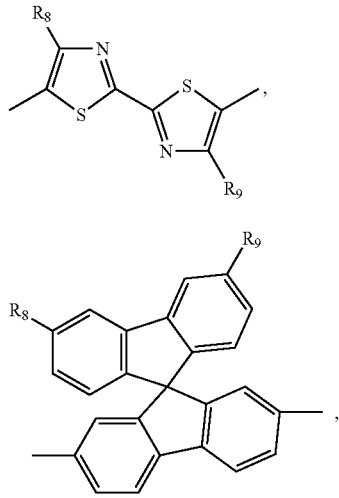

(1o)

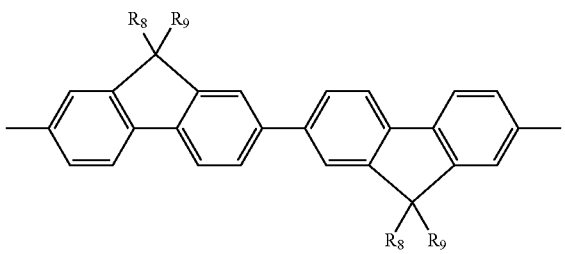

(1q)

wherein each of $R_8$ and $R_9$ is independently selected from the group consisting of a hydrogen atom, a substituted or unsubstituted C1-C12 alkyl group, a substituted or unsubstituted C1-C12 alkoxy group, and a substituted or unsubstituted amino group;

each X is $CH_2$—$CH_2$; and each of $R_1$ through $R_7$ is independently selected from the group consisting of a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C5-C30 heteroaryl group, a substituted or unsubstituted C5-C30 heteroarylalkyl group, a substituted or unsubstituted C5-C30 heteroaryloxy group, a substituted or unsubstituted C5-C20 cycloalkyl group, and a substituted or unsubstituted C5-C30 heterocycloalkyl group.

* * * * *